United States Patent [19]

Widauer

[11] Patent Number: 5,310,560
[45] Date of Patent: May 10, 1994

[54] MEDICINE FOR THE TREATMENT OF ILLNESSES OF THE RESPIRATORY ORGANS

[75] Inventor: Josef O. Widauer, Allschwil, Austria

[73] Assignee: Medichemie AG, Ettingen, Switzerland

[21] Appl. No.: 879,339

[22] Filed: May 5, 1992

[30] Foreign Application Priority Data

May 15, 1991 [CH] Switzerland ............ 1452/91-0

[51] Int. Cl.$^5$ .................... A61K 9/48; A61K 9/30
[52] U.S. Cl. .................... 424/451; 424/456; 424/474; 514/170; 514/182
[58] Field of Search .............. 514/170, 182; 424/451, 424/456, 474

[56] References Cited

U.S. PATENT DOCUMENTS 4,681,876  7/1987  Marple et al. .............. 514/182
4,917,898  4/1990  Angelico et al. .............. 424/452

OTHER PUBLICATIONS

"The Merck Index," 1989, No. 2044.
"The Merck Index," 1989, No. 9801.
Scand J. Rheumatology 4, 169–173, 1975.

*Primary Examiner*—Thurman K. Page
*Assistant Examiner*—Robert H. Harrison
*Attorney, Agent, or Firm*—Tarolli, Sundheim & Covell

[57] ABSTRACT

Chenodeoxycholic acid and ursodeoxycholic acid, both being natural gallic acids, are well known for the treatment of cholesterin gallstones, of biliaric dyspepsia, and also chronic liver diseases (only Urso). The object of the present invention is the use of these acids or a combination thereof for the making of a medicine for treating acute or chronic inflammatory illnesses of the respiratory organs.

9 Claims, No Drawings

MEDICINE FOR THE TREATMENT OF ILLNESSES OF THE RESPIRATORY ORGANS

TECHNICAL FIELD

The present invention relates to the use of gallic acids chenodeoxycholic acid and ursodeoxycholic acid or a combination thereof for the manufacture of a medicine.

The chemical designation of chenodeoxycholic acid is 3α,7α-Dihydroxy-5β-cholan-24-oic-acid. The summation formula is $C_{24}H_{40}O_4$. The structural formula is

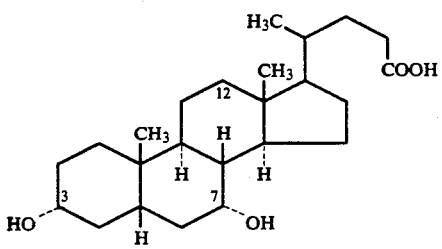

The chemical designation of ursodeoxycholic acid is 3α,7α-Dihydroxy-5β-cholan-24-oic-acid. The summation formula is $C_{24}H_{40}O_4$. The structural formula is

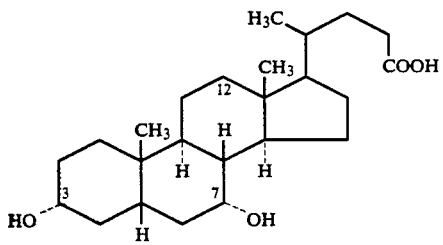

Both gallic acids can be obtained in a part-synthetic process from cattle bile.

STATE OF THE ART

It is known to administer the above-named gallic acids in daily doses between 5-20 mg/kg of body weight in order to dissolve cholesterin gallstones, and also for biliaric dyspepsia. The named gallic acids can be used either by themselves or in combination with one another. Because of somewhat differing effect mechanisms, they show an additive effect in a mixed preparation. Moreover, the ursodeoxycholic acid is also used in the treatment of reflux gastritis as well as in chronic hepatophatia. In connection with these known indications, reference is directed to Ulrich Leuschner: "Aktuelle Aspekte der Therapie mit Gallensäuren", Deutsches Ärtzeblatt 86, Volume 48, C-2180–2186, November, 1989 or Alan F. Hofmann "Medical Dissolution of Gallstones by Oral Bile Acid Therapy", The American Journal of Surgery, Volume 158/Number 3, page 79–85, September 1989.

EXPLANATION OF THE INVENTION

Surprisingly, the above named gallic acids are therapeutically effective also for acute or chronic inflammatory illnesses of the respiratory organs, in particular the upper respiratory passages, for example in chronically obstructed bronchitis, in chronic pharyngitis, or also for chronic tonsillitis.

In a clinical trial for example, for a period of three weeks, on a daily basis, three capsules of ursodeoxycholic acid, each having 250 mg, were administered to three male patients with ages between 53 and 68 years, for whom the uniform diagnosis was chronic asthma-bronchitis. This corresponds to about 10 mg/kg of body weight of the patients. The test parameters before and after the treatment are found in the Table below.

| Subjective and Objective Test Parameters (n = 3) | Evaluation and Grading | |
|---|---|---|
| | Before Urso-Treatment | After Urso-Treatment |
| Irritation cough | +++ | + |
| Sputum | +++ | + |
| Exertional Dyspnea | ++ | + |
| Whistling noises upon auscultation | ++ | + |
| Pathological Spirometra (reduced FEV 1) | ++ | + |
| Disturbed pulmonary gas exchange | ++ | + |
| Pathological Sputum Diagnosis | ++ | 0 |

+++ = strong, ++ = average, + = weak, 0 = absent.

According to the above, based on a controlled investigation, after three weeks of treatment it was possible to note both subjectively and objectively a clear improvement of breathing difficulties. The patients all reported feeling a definite decrease in irritation cough, and especially, decreased sputum. The exertional dyspnea (shortness of breath upon exertion) also subjectively improved. The results of the objective analysis, in agreement with the statements of the patients, confirm an improvement of symptoms:

Regarding spirometra, in all patients there was noted a significant improvement of the FEV 1= Tiffeneau-Test by more than 10% (improvement of breath volume).

The bronchial mixed infection with pathogenic bacteria (*Haemophilus Influenzas,* Pneumococcus) present in the "before" testing, could not be detected during the "after" investigations (this occurring without antibiotic treatment). The sputum eosinophils had also disappeared.

Finally, with all patients, the doctor's auscultation results were clearly improved.

The object of this invention is therefore the use of chenodeoxycholic acid, ursodeoxycholic acid, or a combination of chenodeoxycholic acid and ursodeoxycholic acid to make a medicine for the treatment of acute or chronic inflammatory illnesses of the respiratory organs.

GALENICAL EXAMPLES

The following are several galenical examples for the manufacture of capsules and tablets containing ursodeoxycholic acid, chenodeoxycholic acid or a combination of the two.

EXAMPLE 1

Capsules 25 kg ursodeoxycholic acid were mixed with corn or potato starch, highly dispersed silicon dioxide and magnesium stearate, and placed into 100,000 hard-gelatin capsules each with a content of 250 mg ursodeoxycholic acid.

EXAMPLE 2

Capsules 25 kg of chenodeoxycholic acid were mixed with corn or potato starch, highly dispersed silicon dioxide and magnesium stearate, and placed into 100,000 hard-gelatin capsules, each with a content of 250 mg.

EXAMPLE 3

Capsules 25 kg each of chenodeoxycholic acid and ursodeoxycholic acid were mixed with corn or potato starch, highly dispersed silicon dioxide and magnesium stearate, and placed into 100,000 hard-gelatin capsules, each containing 250 mg of chenodeoxycholic acid and 250 mg of ursodeoxycholic acid.

EXAMPLE 4

Coated Tablets 25 kg of ursodeoxycholic acid were granulated with corn or potato starch, highly dispersed silicon dioxide, milk sugar, powdered cellulose, magnesium stearate and talcum, and pressed into tablets each having a content of 250 mg ursodeoxycholic acid. These tablets were covered with a film of polymers such as cellulose derivates, polymethacryl-acid ester, polyvinyl pyrrolidon, polyethylene glycol.

EXAMPLE 5

Coated Tablets 25 kg of chenodeoxycholic acid were granulated with corn or potato starch, highly dispersed silicon dioxide, milk sugar, powdered cellulose, magnesium stearate and talcum, and pressed into tablets each having a content of 250 mg chenodeoxycholic acid. These tablets were covered with a film, consisting of polymers such as cellulose derivates, polymethacryl-acid ester, polyvinyl pyrrolidon, polyethylene glycol.

EXAMPLE 6

Coated Tablets 25 kg of each of chenodeoxycholic acid and ursodeoxycholic acid were granulated with corn or potato starch, highly dispersed silicon dioxide, milk sugar, powdered cellulose, magnesium stearate and talcum, and pressed into tablets each having a content of 250 mg chenodeoxycholic acid and 250 mg ursodeoxycholic acid. These tablets were covered with a film of polymers such as cellulose derivates, polymethacryl-acid ester, polyvinyl pyrrolidone polyethylene glycol.

In the foregoing examples, the capsules and coated tablets contain either only ursodeoxycholic acid or only chenodeoxycholic acid, each in an amount of 250 mg. When one of the tablets or capsules is administered three times a day, this corresponds, for a person of normal weight (75 kg body weight), to roughly the preferred daily dose of 10 mg/kg of body weight. In the combination preparations, 250 mg of both materials are contained. On the basis of a somewhat differing effect mechanism as between the two materials, suspected due to the indications in accordance with the invention, an additive effect should be attained.

I claim:

1. A pharmaceutical gelatin capsule or polymer coated tablet for the treatment of acute and chronic inflammatory illness of the respiratory organs, comprising as the active principle chenodeoxycholic acid in admixture with suitable carriers or excipients, and a gelatin encapsulating agent or polymer coating to encapsulate or coat said active principle.

2. A method of treating a patient for the therapy of acute and chronic inflammatory illness of the respiratory organs which comprises the administration of an effective amount of said active principle according to claim 1.

3. A pharmaceutical gelatin capsule or polymer coated tablet for the treatment of acute and chronic inflammatory illness of the respiratory organs, comprising as the active principle ursodeoxycholic acid in admixture with suitable carriers or excipients, and a gelatin encapsulating agent or polymer coating to encapsulate or coat said active principle.

4. A method of treating a patient for the therapy of acute and chronic inflammatory illness of the respiratory organs which comprises the administration of an effective amount of said active principle according to claim 3.

5. A pharmaceutical gelatin capsule or polymer coated tablet for the treatment of acute and chronic inflammatory illness of the respiratory organs, comprising as the active principle a combination of chenodeoxycholic acid and ursodeoxycholic acid in admixture with suitable carriers or excipients, and a gelatin encapsulating agent or polymer coating to encapsulate or coat said active principle.

6. A method of treating a patient for the therapy of acute and chronic inflammatory illness of the respiratory organs which comprises the administration of an effective amount of said active principle according to claim 5.

7. A method to improve breathing difficulties for a patient with inflammatory illness of the respiratory organs comprising administering to said patient an effective amount of a gelatin capsule or polymer coated tablet comprising (1) an active principle selected from the group consisting of chenodeoxycholic acid, ursodeoxycholic acid and combinations thereof in admixture with suitable carriers or excipients, and (2) a gelatin encapsulating agent or polymer coating to encapsulate or coat said active principle.

8. A pharmaceutical gelatin capsule or polymer coated tablet comprising (1) an active principle selected from the group consisting of chenodeoxycholic acid, ursodeoxycholic acid and combinations thereof in admixture with suitable carriers or excipients for the treatment of a patient with inflammatory illness of the respiratory organs, and (2) a gelatin encapsulating agent or polymer coating to encapsulate or coat said active principle.

9. A pharmaceutical capsule or coated tablet of claim 8 wherein an effective amount of said active principle is used for the treatment of a patient with symptoms selected from the group consisting of chronically obstructed bronchitis, chronic pharyngitis, chronic tonsillitis and combinations thereof.

* * * * *